United States Patent
Oshima (10) Patent No.: US 7,371,556 B2
(45) Date of Patent: May 13, 2008

(54) MICROORGANISM

(75) Inventor: Tairo Oshima, Tokyo (JP)

(73) Assignee: Kabushiki Kaisha Sanyu, Kagoshima (JP)

( * ) Notice: Subject to any disclaimer, the term of this patent is extended or adjusted under 35 U.S.C. 154(b) by 417 days.

(21) Appl. No.: 10/497,997

(22) PCT Filed: Dec. 24, 2002

(86) PCT No.: PCT/JP02/13424

§ 371 (c)(1),
(2), (4) Date: Jul. 14, 2004

(87) PCT Pub. No.: WO03/055985

PCT Pub. Date: Jul. 10, 2003

(65) Prior Publication Data

US 2005/0032193 A1  Feb. 10, 2005

(30) Foreign Application Priority Data

Dec. 25, 2001 (JP) ............................. 2001-391561

(51) Int. Cl.
- C12N 1/20 (2006.01)
- C12N 1/00 (2006.01)
- C02F 3/34 (2006.01)
- C01N 63/00 (2006.01)

(52) U.S. Cl. .................. 435/252.1; 435/262; 435/267; 435/822

(58) Field of Classification Search ............. 435/252.1, 435/262, 267
See application file for complete search history.

(56) References Cited

U.S. PATENT DOCUMENTS 5,283,189 A * 2/1994 Takase et al. ................ 435/207
5,540,839 A   7/1996 Pirt

FOREIGN PATENT DOCUMENTS

| EP | 0641296 A1 | 7/1996 |
|---|---|---|
| JP | 51-129759 | 11/1976 |
| JP | 55-121992 | 9/1980 |
| JP | 56-154991 | 11/1981 |
| JP | 6-105679 | 4/1994 |
| JP | 6-191977 | 7/1994 |
| JP | 9-059081 | 3/1997 |
| JP | 9059081 A | 3/1997 |
| JP | 2005013063 A | 1/2005 |
| WO | WO 93/04988 A1 | 7/1996 |

OTHER PUBLICATIONS

Bergey's Manuel of Determinative Bacteriology. 9th edition. 1994, pp. 98 and 171.*
Oshima, T., "The Physiology of Polyamines", Bachrach, U., and Heimer, Y. eds) (1989) vol. 2, pp. 35-46., CRC Press,. Boca Raton, FL, US.
Hamana, K. Niitsu, et al., (1991) J. Biochem., 109, pp. 444-449.
Oshima, T., et al. (1987), J. Biol. Chem., 262, 11979-11981.
Oshima, T., (1983) Methods Enz., 94, pp. 401-411.
Brock, "Biology of Microorganisms", 8th ed., Madigan Martinko, Parker, pp. 617-621 (1997).

* cited by examiner

*Primary Examiner*—Vera Afremova
(74) *Attorney, Agent, or Firm*—Greenblum & Bernstein, P.L.C.

(57) ABSTRACT

The present invention relates to a novel hyperthermophile, in particular, to a hyperthermophile belonging to a novel genus isolated from compost by fermenting organic wastes at a temperature of 85° C. or more which is capable of growing at 80° C. or more (*Caldothrix satsumae*). The hyperthermophile of the present invention does not multiply at 50° C. or below, but grows and multiplies vigorously at 70 to 85° C. It is non-spore forming, gram-negative, and an absolutely aerobic rod.

The hyperthermophile is useful as a fermenting microbe when organic wastes are fermented at high temperatures to produce compost. Further the hyperthermopile can be utilized for the production of heat resistant enzymes.

7 Claims, 3 Drawing Sheets

Fig. 6

```
                        SEQUENCE LISTING

<160> NUMBER OF SEQ ID NOS: 1

<210> SEQ ID NO 1
<211> LENGTH: 1520
<212> TYPE: DNA
<213> ORGANISM: Caldothrix satsumae

<400> SEQUENCE: 1
agagtttgat cctggctcag gacgaacgct ggcggcgcgc ctaatacatg caagtcgagc      60
ggggcttttc gcgtgaagcc ttcgggcgga tcgcggggag agcctagcgg cgaacgggtg     120
cgtaacacgt gggcaaccta ccccgaggac cgggataact ccgggaaacc ggggctaata     180
ccggatagga cggcggaccg catggtccgc cgtggaaagg cggcgcaagc tgccacctcg     240
ggatgggccc gcggcccatt agcttgttgg tggggtaacg gcccaccaag gcgacgatgg     300
gtagccggcc tgagagggtg accggccaca ctgggactga gacacggccc agactcctac     360
gggaggcagc agtagggaat cttccgcaat gggcgaaagc ctgacggagc gacgccgcgt     420
gagggaggaa ggccttcggg tcgtaaacct ctgttgtcag gacgaaccc gtgcggttcg      480 aagagggccg cgcgctgacg gtacctgacg aggaagcccc ggctaactac gtgccagcag     540
ccgcggtaaa acgtagggggg cgagcgttgt ccggaattac tgggcgtaaa gcgcgcgtag     600
gcggcctctt aagtccggtg tgaaagcccg cggctcaacc gcgggaggcc actggaaact     660
gggaggcttg agggcaggag aggggagtgg aattcccggt gtagcggtga aatgcgtaga     720
gatcgggagg aacaccagtg gygaaggcgg ctccctggcc tgtacctgac gctgaggcgc     780
gaaagcgtgg ggagcaaaca ggattagata ccctggtagt ccacgccgta aacgatgggt     840
gctaggtgtg aggggcgttt ggcccttcgt gccgaagcta acgcgataag cacccgcct      900 ggggagtacg gccgcaaggc tgaaactcaa aggaattgac gggggcccgc acaagcggtg     960
gagcatgtgg tttaattcga agcaacgcga agaaccttac cagggcttga catcccgctg    1020
accgccccag agatgggggtt tccctccttt cggagggcag cggtgacagg tggtgcatgg    1080
ttgtcgtcag ctcgtgtcgt gagatgttgg gttaagtccc gcaacgagcg caaccctgc     1140 ccctagttgc cagcgggtga ggccgggcac tctaggggga ctgccggcga caagccggag    1200
gaaggtgggg atgacgtcaa atcatcatgc cccttatgcc ctgggctaca cacgtgctac    1260
aatggccggt acaaagggtt gcgaacccgc gaggggagc caatcccaaa aagccggtct    1320
cagttcggat tgcaggcttg caactcgcct gcatgaaggc ggaatcgcta gtaaatccgc    1380
gggatcagca tgccgcggtg aatacgttcc cgggccttgt acacaccgcc cgtcacacca    1440
cgagagtctg caacacccga agtcggtgcg ccaaccccttt acggggaggc agccgccgaa    1500
ggtggggcag atgattgggg                                                 1520
```

MICROORGANISM

This application is a 371 national stage application of PCT/JP02/13424 filed Dec. 24, 2002, which claims priority of JP 391561/2001 filed Dec. 25, 2001.

TECHNICAL FIELD

The present invention relates to a novel hyperthermophile derived from compost that can multiply at 80° C. or more.

BACKGROUND ART

Heretofore, thermophilic microbes have been made to act on organic wastes such as droppings of domestic animals, excrement and urine, sludge, and city waste to aerobically ferment the wastes and to make them odorless and dry, thereby preparing compost. Further, as such thermophilic microbes, there have been known thermophilic actinomycetes belonging to the genera *Thermoactinomyces* or *Thermomonospora* (JP 55-121992 A), a mixture of thermophilic, aerobic and spore-forming bacteria such as those belonging to the genera *Bacillus* or *Geobacillus* or lactic acid-producing bacteria (JP 51-129759 A), aerobic *Bacillus subtilis* (JP 6-5197 A), bacteria belonging to the genus *Thermus aquaticus* having lignin-solubilizing capability (JP 6-105679 A), aerobic cellulose degrading bacteria *Clostridium thermocellum*, *Thermus aquaticus* (JP 6-191977) and so forth.

However, in spite of use of these microbes, although the fermentation temperature is elevated to 70° C. or more due to fermentation heat at the time of fermentation, the temperature is elevated up to 80° C. at the most, and thus, saprophytes, in particular, spore-forming saprophytes could not be extinguished. In addition, the number of useful bacteria cells in the obtained fertilizer is at most around 100,000,000 per g (dry fertilizer), so that when the cells are used as a fertilizer, the fertilizing effect could not be exhibited sufficiently.

To solve these problems regarding the disposal of sludge, the inventors of the present invention have made intensive studies to obtain a fermented product which purifies the sludge by subjecting the sludge to fermentation treatment at high temperatures of 85° C. or more, more preferably 95° C. or more, to extinguish saprophytes, seed of weeds, and the like, and which contains a large number of useful bacteria cells. As a result, the inventors found a method of obtaining a fermented sludge product containing a large number of solely the useful bacteria cells, comprising: adding a culture of a bacterium that grows at temperatures not lower than 85° C. obtained from the soil of Kirishima volcanic region in the prefecture of Kagoshima, Japan to raw sludge and mixing them; and subjecting the resulting mixture to aerobic fermentation to extinguish the saprophytes and seeds contained in the sludge at a fermentation temperature of 85° C. or more to purify the sludge, and have obtained a patent on the method (JP 3064221 B). And, the fermented sludge has been used as compost, in which mesophilic aerobic spore-forming bacteria, thermophilic aerobic, spore-forming bacteria, thermophiles and the like belonging to the genera *Bacillus* or *Geobacillus* have been found in large numbers.

That is, about 1,000,000,000 bacteria cells are included per g of the fermented sludge, the bacteria predominantly including aerobic bacteria, thermophilic bacteria and thermodulic spores as shown in Table 1.

TABLE 1

| Subject bacterium | Number of viable bacteria cells per g |
|---|---|
| Aerobic bacteria | $9.9 \times 10^8$ |
| Thermophilic bacteria | $8.4 \times 10^7$ |
| Thermodulic spores | $2.8 \times 10^7$ |
| Enterobacteria | 100 or less |
| Gram-negative bacteria | 100 or less |
| Gram-positive bacteria | $2.8 \times 10^6$ |
| Lactic acid bacteria | 100 or less |
| Anaerobic bacteria | 100 or less |
| Mesophilic actinomycetes | $1.1 \times 10^3$ |
| Thermophilic actinomycetes | $6.0 \times 10^2$ |
| Filamentous fungi | 100 or less |
| Yeast | 100 or less |

On the other hand, in the culture, a colony that grew dominantly on the culture plate was selected to obtain an isolated bacterium, and the isolated bacterium was subjected to morphological observation and the like in order to searched for microbes that may be concerned with fermentation. As a result, it was revealed that the following microbes are concerned with the fermentation.

TABLE 2

| Isolated bacterium group | Number of viable bacteria cells per g |
|---|---|
| Polymorphic, sporeless gram-positive *bacillus* | $7 \times 10^2$ |
| Aerobic spore-forming bacteria | |
| mesophilic | $3 \times 10^8$ |
| thermophilic | $8 \times 10^7$ |
| Catalase-positive gram-positive cocci | $1 \times 10^7$ |
| Actinomycetes | |
| mesophilic | $1 \times 10^3$ |
| thermophilic | $6 \times 10^2$ |

As described above, it was revealed that mainly polymorphic, sporeless gram-positive *bacilli*, aerobic spore-forming bacteria (mesophilic and thermophilic) are involved.

On the other hand, measurement of thermophiles was performed referring to the description in, "Methods for Isolating Microbes", YAMAZATO, Kazuhide and three others, ed., published by R&D Planning. The dominant thermophile was aerobic spore-forming bacteria (thermophilic).

Further, the mesophilic aerobic spore-forming bacterium (isolated bacterium a), thermophilic aerobic spore-forming bacterium (isolated bacterium b), and thermophile (isolated bacterium c) that were isolated predominantly in the above-mentioned search of microbes were subjected to morphological observation, physiological property tests and measurement of the GC content of DNA in bacterial cell. The results obtained are shown in Table 3.

TABLE 3

| | Test result | | |
|---|---|---|---|
| Test Item | Isolated bacterium a | Isolated bacterium b | Isolated bacterium c |
| Morphology | rod | rod | rod |
| Gram stain | + | + | + |
| Spore | + | + | + |
| Shape | Circular to ellipsoidal | Ellipsoidal | Ellipsoidal |

TABLE 3-continued

|  | Test result | | |
| --- | --- | --- | --- |
| Test Item | Isolated bacterium a | Isolated bacterium b | Isolated bacterium c |
| Site | Central | Quasi-peritrichous | Quasi-peritrichous to peritrichous |
| Sporangium | Not swollen | Swollen | Not swollen to slightly swollen |
| Motility | – | – | + |
| Behavior toward enzymes | Aerobic | Aerobic | Aerobic |
| Catalase | + | + | + |
| Growth under anaerobic conditions | – | – | – |
| V-P reaction | – | – | – |
| pH of V-P broth | 6.5 | 8.0*[2] | 5.6 |
| Acid formation | | | |
| Glucose | – | –*[2] | – |
| Arabinose | NT* | –*[2] | NT* |
| Xylose | NT* | –*[2] | NT* |
| Mannitol | NT* | –*[2] | NT* |
| Gas formation from glucose | – | –*[2] | – |
| Casein decomposition | + | – | NT* |
| Gelatin salination | + | – | + |
| Starch decomposition | – | – | – |
| Assimilation of citrate | – | –*[2] | – |
| Assimilation of propionate | – | –*[2] | – |
| Tyrosine decomposition | – | – | – |
| Phenylalanine deamination | – | NT* | NT* |
| Egg yolk reaction | – | – | – |
| Nitrate reduction | + | – | – |
| Growth at pH 6.8 (Nutrient broth) | + | – | + |
| Growth at pH 5.7 | – | – | – |
| Growth in the presence of 5% NaCl | + | + | – |
| Growth in the presence of 7% NaCl | + | + | – |
| Growth at 10° C. | – | – | NT* |
| Growth at 30° C. | + | slow | – |
| Growth at 40° C. | + | + | + |
| Growth at 50° C. | – | + | NT* |
| Growth at 55° C. | NT* | + | + |
| Growth at 65° C. | NT* | – | + |
| Growth at 70° C. | NT* | NT* | + |
| Growth at 71° C. | NT* | NT* | + |
| Growth at 72° C. | NT* | NT* | – |
| GC content of cell DNA (mol %) | 52*[1] | 52*[1] | 40*[1] |

*NT: No test performed;
*[1]By an HPLC method;
*[2]Medium adjusted to pH 8.0 being used.

The isolated bacterium a did not correspond to any of the species in respect of the properties so that its species was not identified. The isolated bacterium b showed good growth on a slightly alkaline medium (pH 8.0 to 8.5) but did not grow on a medium at pH 7.0, and the results of tests on other properties suggested that it was a species close to *Bacillus badius* or *B. brevis*. However, bacterium b has properties which are non-typical to either of them, so that no identification of species was attained. Further, because the isolated bacterium c showed bacteriological properties identical to those of *Geobacillus stearothermophilus*, it may be identified as the same species. However, a great difference in their GC contents suggested that they are closely-related species.

These isolated bacteria have been deposited at Agency of Industrial Science and Technology, National Institute of Bioscience and Human-Technology (presently, International Patent Organism Depository, National Institute of Advanced Industrial Science and Technology), where accession numbers were respectively assigned: YM-01 accession number FERM P-15085 for the isolated bacterium a, YM-02 accession number FERM P-15086 for the isolated bacterium b, and YM-03 accession number FERM P-15087 for the isolated bacterium c.

The inventors of the present invention further made studies on the presence of such microbes that grow at high temperatures in compost and have surprisingly found a hyperthermophile belonging to a new genus that vigorously multiplies at high temperatures of 75° C. or more, still shows its multiplication at 85° C. but shows no multiplication at 50° C. or less.

DISCLOSURE OF THE INVENTION

An object of the present invention is to obtain a novel thermophile, in particular, a hyperthermophile from compost obtained by fermenting sludge at 85° C. or more.

In order to solve the above-mentioned problems, the inventors of the present invention have attempted to search for thermophilic microbes that exist in the compost obtained by fermenting the sludge at 85° C. or more (trade name Satsuma Soil; manufactured by the Bureau of Waterworks Department, Kagoshima City) and as a result, the inventors have found an absolutely aerobic bacterium that does not multiply at a culture temperature for ordinary bacteria (30 to 40° C.) but vigorously grows and multiplies at 70 to 85° C., in particular, at 80° C. or more. The inventors then carried out phylogenetic systematics analysis on the bacterium based on the nucleotide sequence of 16S rDNA. As a result, the inventors of the present invention have found that although this absolutely aerobic bacterium is gram-negative and has no capability of spore-formation, it is close to the gram-positive soil bacteria belonging to the genera *Bacillus* or *Geobacillus* but it is a bacterium that is independent from these bacteria on the level of at least genus. The inventors of the present invention named the bacterium *Caldothrix satsumae* YM081 and deposited it at International Patent Organism Depository, National Institute of Advanced Industrial Science and Technology and, where an accession number FERM P-18598 was assigned. Thereafter, the bacterium was transferred to the international depositary, where an accession number FERM BP-8233 was assigned.

That is, the present invention, relates to a novel hyperthermophile belonging to the genus *Caldothrix* that multiplies at 80° C. or more.

The present invention relates to a novel hyperthermophile that belongs to *Caldothrix satsumae*.

In particular, the present invention relates to *Caldothrix satsumae* YM081 strain (FERM BP-8233), which is a novel hyperthermophile.

Further, the entire nucleotide sequence of 16S rDNA of this bacterium has a nucleotide sequence as shown in SEQ ID. No. 1 in the sequence listing.

BEST MODE FOR CARRYING OUT THE INVENTION

The hyperthermophile of the present invention was isolated from the compost (trade name Satsuma Soil) obtained by fermenting organic wastes such as excrement and urine from Kagoshima City, Kagoshima prefecture, Japan at high temperatures in accordance with the method described in JP 3064221 B. As the method of isolation, the following method was used.

To 5 ml of a medium having the composition described in Table 4 below was added about 0.1 g of the above-mentioned compost. Subculturing was repeated while maintaining the temperature at 80° C. to enrich the bacterium, and then isolation and purification thereof were repeated on a plate containing the same medium as described above to which gellan gum was added.

TABLE 4

| | |
|---|---|
| Soluble starch | 0.1 g |
| Casein | 0.3 g |
| NaCl | 5 g |
| Yeast extract | 0.2 g |
| Water | 100 ml |
| | pH 7.2 |

The microbiological properties and taxonomical position of the bacterium thus obtained were as follows.

Figure 1:
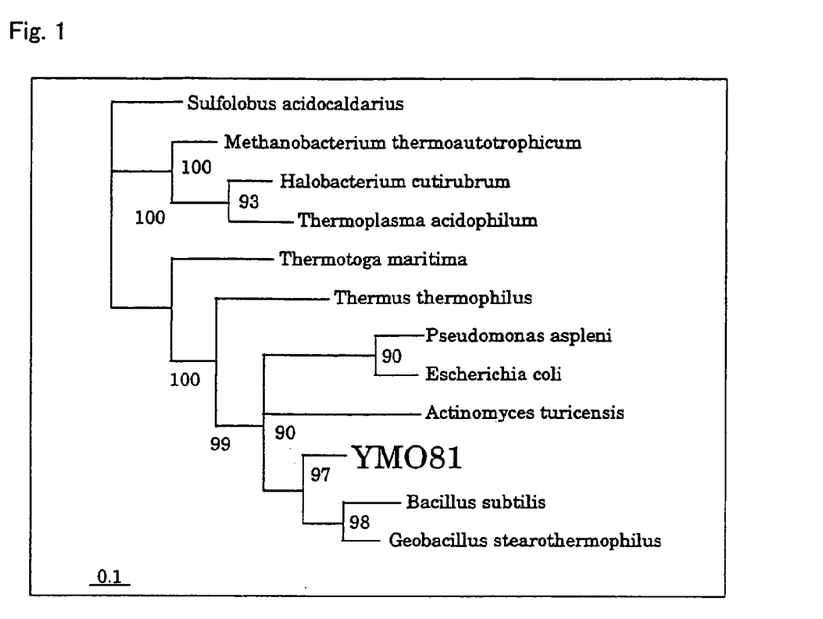
FIG. 1 is a phylogenetic tree of the genus *Caldothrix* of the present invention based on 16S rDNA. Note that in FIG. 1, YM081 indicates *Caldothrix satsumae* YM081 strain, the hyperthermophile of the present invention.
Figure 2:
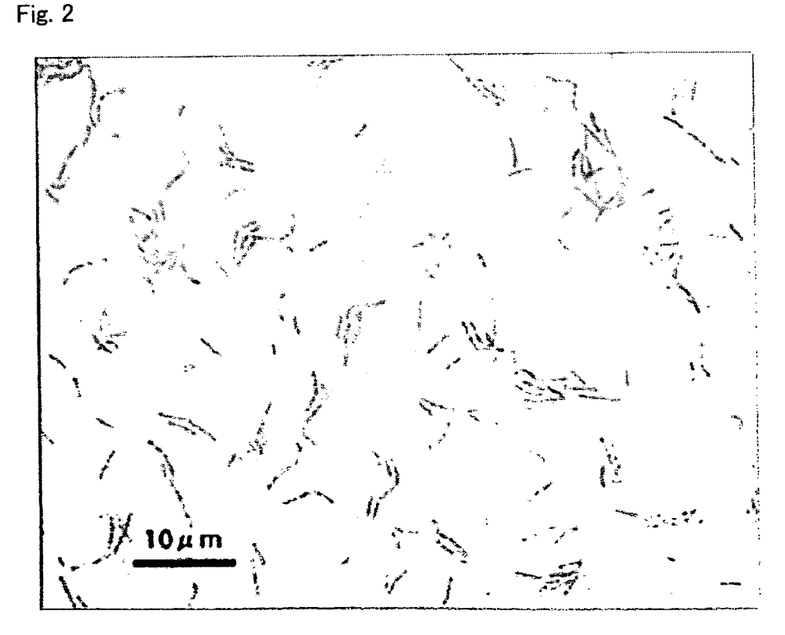
FIG. 2 is an optical micrograph of *Caldothrix satsumae* YM081 strain of the present invention.
Figure 3:
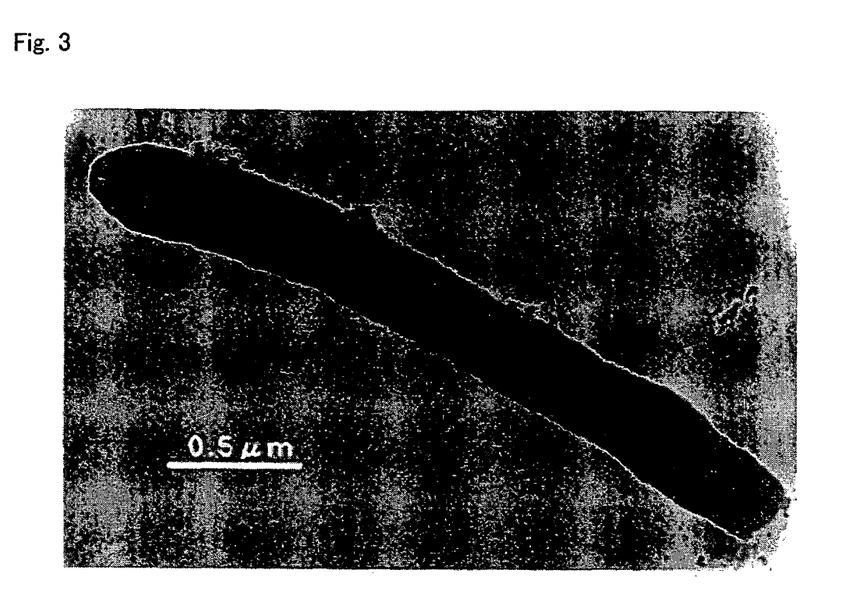
FIG. 3 is a scanning electron micrograph of *Caldothrix satsumae* YM081 strain of the present invention.
Figure 4:
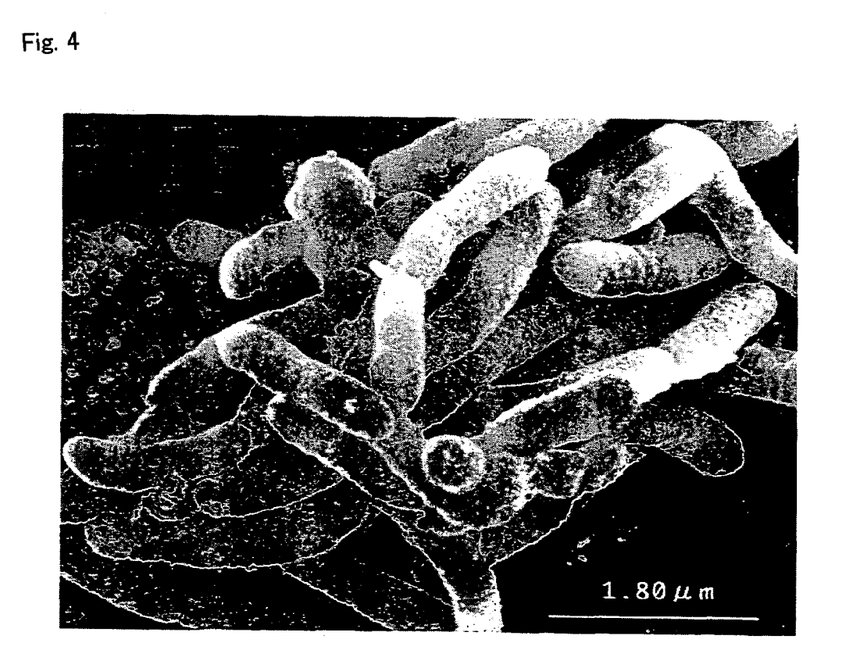
FIG. 4 is a transmission electron micrograph of *Caldothrix satsumae* YM081 strain of the present invention.
Figure 5:
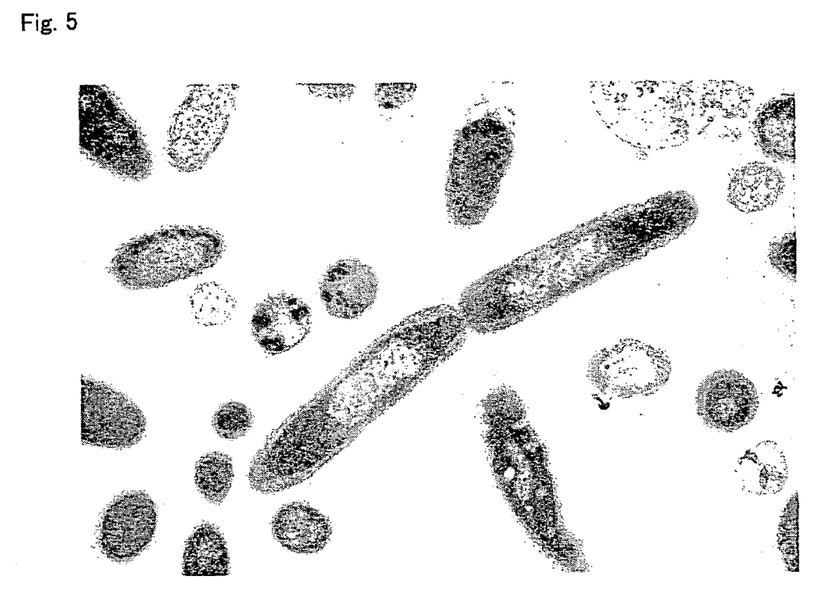
FIG. 5 is an electron micrograph (magnification 5,000 times) of an ultrathin section of a cell of *Caldothrix satsumae* YM081 strain of the present invention.

1) Morphologically, it is a long *bacillus* having a width of 0.5 μm and a length of 3 μm. The results of gram stain were negative. The electron microscopic observation of an ultrathin section of the microbial cell also indicated that the surface structure of the cell is of the gram-negative type, that is, existence of an outer membrane besides cell membrane (plasma membrane) and cell wall was observed. It has no spore formation capability.
2) It grows vigorously at 70 to 85° C.; at 50° C. or less, no growth is observed. At high temperatures of 75° C. or more, it multiplies vigorously and even at 85° C., multiplication is observed. It is an obligate aerobe.
3) Optimal pH for multiplication is neutral. The pH range in which it can multiply is 6 to 9. Also, it shows weak halophilism.
4) It shows assimilability of various proteins such as albumin and casein as well as starch.
5) It has urease productivity but no nitrate reduction capability. It has no hydrogen sulfide productivity or indole productivity.
6) The G+C content of DNA is 70.0%.
7) Phylogenetic systematics analysis based on the nucleotide sequence of 16S rDNA was performed. The results are shown in FIG. 1 and Table 6. Further, the entire nucleotide sequence of 16S rDNA was shown in SEQ ID No. 1 in the sequence listing.

As described above, the bacterium of the present invention is close to the genera *Bacillus* or *Geobacillus* of gram-positive soil bacteria having spore-formation capability although the bacterium is gram-negative and has no spore formation capability. However, the bacterium is independent of these bacteria on the level of at least genus.

From these, it was revealed that the microbe of the present invention belongs to Eubacteriales and is a hyperthermophile. Also, from the nucleotide sequence of 16S rDNA, it was revealed that the microbe is close to *Geobacillus stearothermophilus* but forms a genus independent thereof.

EXAMPLES

The present invention will be described by way of reference examples and examples as follows. However, the present invention should not be construed as being limited to these reference examples and examples.

Reference Example 1

1. Preparation of Cell Culture

The soil at 37 to 40° C. of a sulfur zone in the Kirishima volcanic belt in Makizono town, Aira county, Kagoshima prefecture, Japan and the soil in a paddy field near thereto where green lichens grow were mixed. To the mixture was added an aqueous sucrose solution in an amount of 3 to 4 liters/m$^3$, the sucrose solution being obtained by dissolving sucrose in water that was 500 to 1,000 times the volume of the sucrose The resultant mixture was cultivated by being left at 40 to 50° C. for 30 to 50 days. Aliquots of the culture were mixed with raw sludge in several lots, which then were allowed to be fermented under aerobic conditions with air blowing therein. The lot that had a fermentation temperature of 85° C. or more was adopted as a cell culture.

2. Treatment of Raw Sludge

To a mixture of droppings of animals, sludge from sewage, tailing starch, and kitchen garbage was added slaked lime to carry out deodorant treatment. Then, 80 parts by weight of aliquot thereof was mixed with 20 parts by weight of the cell culture obtained in the above step 1 and fermentation was performed in a fermentation tank under aerobic conditions. By doing so, the temperature of the fermented product increased from room temperature to 85 to 95° C. within a day. At this temperature, the fermentation was maintained for about 3 days, and on 5$^{th}$ day from the start of the fermentation, the product was scrambled up (mixed). As a result of the mixing, the temperature of the fermented product decreased to around 60° C. but in about 1 day, it increased to 85 to 95° C. The fermentation was continued while keeping this temperature for 5 days By repeating the operations of the fermentation and mixing several times, the temperature of the fermented product at the time of mixing and the fermentation temperature were gradually decreased. The day when the temperature of the fermented product at the time of mixing decreased to about 35° C. after repeating these operations four times was defined as the final fermentation day. The obtained fermented product was dried to form brown granules, which could be used as an organic fertilizer.

3. Preparation of Raw Material Compost 80 parts by weight of raw sludge obtained by subjecting the sludge from public sewage in Kagoshima city, Kagoshima prefecture, Japan to compression dehydration to reduce the water content thereof to 68%, and 20 parts by weight of the cell culture obtained in the above step 2 were mixed. The mixture was charged in a fermentation yard where air was blown from bottom to perform fermentation. On the 7$^{th}$ day from the start of fermentation, the temperature reached to 98° C. After the fermentation was performed for 10 days, when the fermentation temperature began to decrease from 98° C., mixing was performed to allow the fermentation to proceed again. After the temperature of 99° C. was first reached, i.e., on 10th day from the mixing, the temperature abruptly decreased to 60 to 70° C. At this point, the fermentation product was spread in the fermentation yard to cool rapidly to ambient temperature to obtain brown fermented sludge powder. The fermented sludge powder can be used as compost, or cell culture or medium for performing the above-mentioned fermentation.

Example 1

Isolation of Hyperthermophile

About 0.1 g of the compost obtained in Reference Example 1 was inoculated in 5 ml of the medium described in Table 4 and repeatedly transplanted and cultured at 80° C. to enrich the bacterium. Thereafter, isolation and purification of the bacterium was carried out repeatedly on plates containing the medium having the same composition as described above to which gellan gum was added to obtain the hyperthermophile of the present invention.

Note that the compost sample was added to peptone/yeast extract medium (0.5% peptone, 0.3% yeast extract, pH 7.2) and the resultant mixture was cultivated at 70° C., followed by isolation of the multiplied bacteria cells on an agar plate (pH 7.2, 70° C.). As a result, *Geobacillus stearothermophilus* that was heretofore believed to be responsible for the fermentation of the compost at a temperature of 70° C. or more and a number of other novel thermophiles were found.

Example 2

Microbiological Properties of Hyperthermophile

The hyperthermophile of the present invention obtained in Example 1 was inoculated in an agar medium with pH 7 to 8 containing 0.3% casein, 0.2% yeast extract, 0.1% starch, and 5% NaCl, and cultivated at 80° C. for 24 hours, followed by examination of the microbiological properties. The results obtained are shown in Table 5.

The microscope images of the hyperthermophile are shown in FIGS. 2 to 5.

TABLE 5

| Test Item | Test result |
| --- | --- |
| Morphology | Long *bacillus* (width 0.5 μm, length 3 μm) |
| Gram stain | Negative |
| Spore formation capability | Not observed |
| Motility | Not observed |
| Behavior toward molecular oxygen | Absolute aerobic |
| Growth under anaerobic conditions | Does not multiply |
| Temperature dependence of Growth | Vigorously grows at 70 to 85° C. but no multiplication is observed at 50° C. or less. Multiplication is observed even at 85° C. or more. |
| Growth pH | Neutral (multiplication is possible at pH 6 to 9) |
| Salt requirement for the growth | Weakly halophilic (optimal NaCl concentration 5%) |
| Albumin decomposition | + |
| Casein decomposition | + |
| Decomposition of sugars and the related compounds | |

TABLE 5-continued

| Test Item | Test result |
| --- | --- |
| Glycerol | + |
| Erythritol | − |
| D-Arabinose | − |
| L-Arabinose | − |
| Ribose | + |
| D-Xylose | − |
| L-Xylose | − |
| Adonitol | − |
| β-Methyl-D-xyloside | − |
| Galactose | − |
| Glucose | + |
| Fructose | + |
| Mannose | ± |
| Sorbose | − |
| Rhamnose | − |
| Dulcitol | − |
| Inositol | − |
| Mannitol | ± |
| Sorbitol | − |
| α-Methyl-D-mannoside | − |
| α-Methyl-D-glucoside | − |
| N-Acetyl-glucosamine | − |
| Amygdalin | − |
| Albutin | − |
| Esculin | + |
| Salicin | − |
| Cellobiose | + |
| Maltose | + |
| Lactose | − |
| Melibiose | − |
| Sucrose | + |
| Trehalose | − |
| Inulin | − |
| Melezitose | ± |
| Raffinose | − |
| Starch | + |
| Glycogen | − |
| Xylitol | − |
| Gentiobiose | − |
| D-Turanose | − |
| D-Lycose | − |
| D-Tagatose | − |
| D-Fucose | − |
| L-Fucose | − |
| D-Arabitol | − |
| L-Arabitol | − |
| Gluconate | − |
| 2-Ketogluconate | − |
| 5-Ketogluconate | − |
| Arabinose | + |
| Nitrate reduction | − |
| Acetoin production | − |
| Hydrogen sulfide formation | − |
| Indole formation | − |
| GC content of chromosomal DNA (mol %) | 70.0 |
| Others | The entire nucleotide sequence of 16 S rDNA was determined and based on this, a molecular phylogenetic tree was constructed. The results are shown in FIG. 1 and Table 6. |

TABLE 6

| | C. satsumae | A. turicensis | B. subtilis | E. coli | G. stearothermophilus | P. aspleni | T. maritima | T. thermophilus |
|---|---|---|---|---|---|---|---|---|
| Caldothrix. satumae | | 78 | 85 | 77 | 85 | 76 | 80 | 78 |
| Actimomyces turicensis | | | 77 | 74 | 75 | 74 | 74 | 74 |
| Bacillus subtilis | | | | 78 | 87 | 79 | 77 | 76 |
| Escherichra coli | | | | | 75 | 85 | 74 | 75 |
| Geobacillus stearothermophilus | | | | | | 74 | 56 | 76 |
| Pseudomonas aspleni | | | | | | | 75 | 75 |
| Thermotoga maritima | | | | | | | | 79 |
| Thermus thermophilus | | | | | | | | |

As a result, it was elucidated that although the bacterium of the present invention belongs to Eubacteriales, is gram-negative and has no spore formation capability, the isolate is closely related to the gram-positive soil bacteria which has spore formation capability and belongs to the genera *Bacillus* or *Geobacillus*, however the isolate is not mono phyletic with them and it thus belongs to a novel genus. Further, as for the GC content of DNA, there was no bacterium that showed 90% or more sequence homology to the base sequence of the 16S rDNA of *C. satsumae* YM081 as shown in Table 1, and the bacterium of the present invention was equidistantly (each 85%) remote from the two genera, i.e., *Bacillus* and *Geobacillus*, so that it was determined to be a novel genus (see Table 6 and FIG. 1). Thus, this genus was named *Caldothrix*. Since the optimal multiplication temperature is 80° C., this bacterium was revealed to be a hyperthermophile.

Note that comparison of biochemical properties between *Caldothrix satsumae* YM081 of the present invention and *Bacillus subtilis* are as shown in Table 7.

TABLE 7

| | YM081 | B. subtilus |
|---|---|---|
| Oxidase activity | − | − |
| Hydrogen sulfide productivity | − | − |
| Galactosidase activity | + | + |
| Leucine fermentability | − | − |
| Acetoin productivity | − | + |
| Indole productivity | − | − |
| Citric acid utilization | + | + |
| Lysine utilization | − | − |
| Ornithine utilization | − | − |
| Arginine utilization | − | − |
| Urea decomposability | + | − |
| Malonic acid utilization | − | − |
| Nitrate reduction | − | + |

The above-mentioned bacterium belonging to a novel genus of the present invention was named *Caldothrix satsumae* YM081 strain and deposited at International Patent Organism Depository, National Institute of Advanced Industrial Science and Technology, and where an accession number FERM P-18598 was assigned. Thereafter, the bacterium was transferred to an international depository, where an accession number FERM BP-8233 was assigned.

Example 3

Relationship Between Temperature and Growth of *Caldothrix Satsumae* YM081 Strain

*Caldothrix satsumae* YM081 strain was inoculated in media comprising starch/casein/yeast extract and subjected to shaking culture at 120 rpm at respective predetermined temperatures and doubling time (time until the number of cells are doubled) was measured. The results are shown in FIG. 6.

Figure 6:
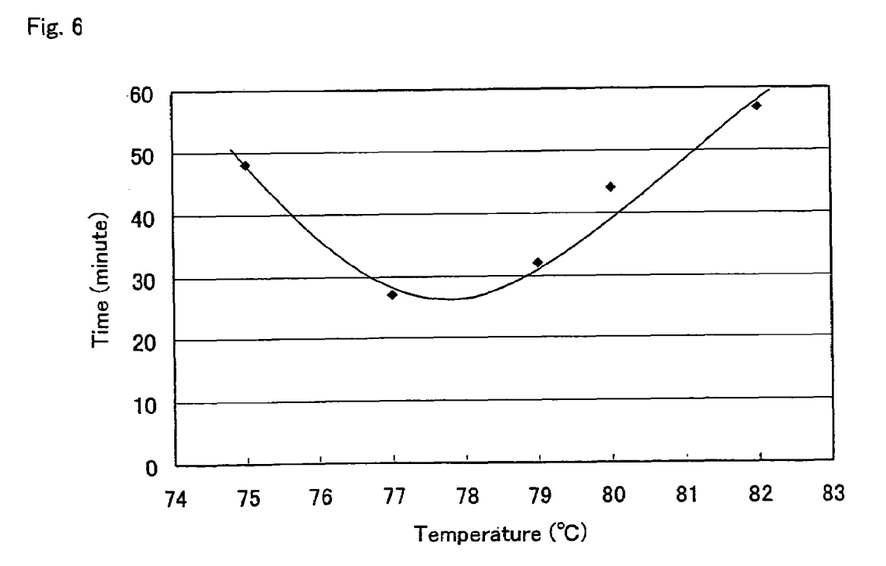
FIG. 6 is a graph showing temperature-dependent generation time of *Caldothrix satsumae* YM081 strain of the present invention.

As apparent from FIG. 6, the optimal multiplication temperature of the bacterium was 78° C. The doubling time at 78° C. was about 26 minutes while the doubling time at 82° C. was about 55 minutes, and even at 82° C., the bacterium continued to multiply with one half of rate under the optimal condition.

Further, adding aqueous solution extracted from the compost to the medium enabled multiplication even at 85° C. as shown in Table 8.

TABLE 8

| Culture temperature | Without extracted solution | With addition of extract solution* |
|---|---|---|
| 80° C. | +++ | +++ |
| 85° C. | − | ++ |

*Extracted solution was added to the medium shown in Table 4.

INDUSTRIAL APPLICABILITY

When the fermentation culture is inoculated to organic wastes such as excrement and urine as a raw material to perform fermentation, the fermentation temperature increases due to a number of mesophiles belonging to the genera *Bacillus* or *Geobacillus*. Thereafter, as the fermentation temperature increases, the hyperthermophile, *C. satsumae* of the present invention begins to participate in the decomposition and fermentation of the organic wastes. Therefore, the hyperthermophile of the present invention is advantageously utilized as, for example, a seed bacterium or medium for decomposing and fermenting the organic wastes at high temperatures to produce compost.

Further, protease and amylase produced by the hyperthermophile have activities at high temperatures and hence production of heat resistance enzymes by utilizing this property is expectable.

Remarks to Deposited Biological Materials

A. Name and address of the organization in which the biological materials have been deposited:
Name: International Patent Organism Depository, National Institute of Advanced Industrial Science and Technology Address: Postal Code: AIST Tsukuba Central 6,1-1, Higashi 1-Chome, Tsukuba-shi, Ibaraki-ken, 305-8566, Japan.

B. Date of deposition to the organization A:
Nov. 7, 2002
(Date of original deposition: Nov. 13, 2001)

C. Number of deposition given by the organization A:
FERM BP-8233

The invention claimed is:

1. An isolated hyperthermophilic bacterium *Caldothrix satsumae* YM081 (FERM BP-8233).

2. An isolated hyperthermophilic bacterium according to claim 1, having the entire 16S rDNA nucleotide sequence of SEQ ID NO. 1.

3. An isolated hyperthermophilic bacterium having a 16S rDNA nucleotide sequence as shown in SEQ ID NO. 1, said bacterium belonging to the genus *Caldothrix* and capable of multiplying at 80° C. or more which is *Caldothrix satsumae* YM081 (FERM BP-8233).

4. A method for producing compost comprising fermenting organic waste at a temperature of at least 85° C. with medium including a hyperthermophilic bacterium as claimed in claim 1.

5. A method for producing compost comprising fermenting organic waste at a temperature of at least 85° C. with medium including a hyperthermophilic bacterium belonging to the genus *Caldothrix* that is capable of multiplying at 80° C. or more but not at 50° C. or less, said bacterium being aerobic, gram negative, and incapable of spore formation, wherein said hyperthermophilic bacterium is *Caldothrix satsumae* YM081 (FERM BP-8233).

6. A method for producing compost according to claim 5 wherein said hyperthermophilic bacterium decomposes starch.

7. A method for producing compost according to claim 5 wherein said hyperthermophilic bacterium has the entire 16S rDNA nucleotide sequence of SEQ ID NO. 1.

* * * * *